US008420595B2

(12) United States Patent
Kopke et al.

(10) Patent No.: US 8,420,595 B2
(45) Date of Patent: Apr. 16, 2013

(54) METHODS FOR TREATING ACUTE ACOUSTIC TRAUMA

(75) Inventors: Richard Dana Kopke, Oklahoma City, OK (US); Robert A. Floyd, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 341 days.

(21) Appl. No.: 12/374,970

(22) PCT Filed: Jul. 25, 2007

(86) PCT No.: PCT/US2007/016758
§ 371 (c)(1),
(2), (4) Date: Jun. 24, 2009

(87) PCT Pub. No.: WO2008/013866
PCT Pub. Date: Jan. 31, 2008

(65) Prior Publication Data
US 2010/0022458 A1    Jan. 28, 2010

Related U.S. Application Data

(60) Provisional application No. 60/833,114, filed on Jul. 25, 2006, provisional application No. 60/833,452, filed on Jul. 26, 2006.

(51) Int. Cl.
*A61K 38/06*    (2006.01)
*A61K 31/15*    (2006.01)
*A61K 31/195*   (2006.01)
*A61K 38/00*    (2006.01)
*A61K 31/41*    (2006.01)
*A61P 27/16*    (2006.01)

(52) U.S. Cl.
USPC ............. 514/2.3; 514/359; 514/563; 514/640

(58) Field of Classification Search .................. 514/18.2
See application file for complete search history.

(56) References Cited

U.S. PATENT DOCUMENTS

| 3,849,934 | A | * | 11/1974 | Dorschner et al. ............ 504/100 |
| 5,143,539 | A | * | 9/1992 | Lovell ........................... 504/103 |
| 5,488,145 | A | | 1/1996 | Carney | |
| 6,337,320 | B1 | * | 1/2002 | Hersh et al. .................... 514/9.4 |
| 2002/0193285 | A1 | | 12/2002 | Hesson et al. | |
| 2003/0082101 | A1 | * | 5/2003 | Taylor et al. ................. 424/1.11 |
| 2004/0053851 | A1 | | 3/2004 | Chabrier de Lassauniere et al. | |
| 2004/0247570 | A1 | | 12/2004 | Miller et al. | |

FOREIGN PATENT DOCUMENTS

| GB | 2414665 | 7/2005 |
| WO | WO92/22290 | 12/1992 |
| WO | WO 2004/096256 | 11/2004 |

OTHER PUBLICATIONS

Szeto; "Mitochondria-Targeted Peptide Antioxidants: Novel Neuroprotective Agents"; The AAPS Journal 2006; 8(3) Article 62; E521-531.
Thomas et al; "Mitochondrial Targeting with Antioxidant Peptide SS-31 Prevents Mitochondrial Depolarization, Reduces Islet Cell Apoptosis, Increases Islet Cell Yield, and Improves Posttransplantation Function"; J Am Soc Nephrol Dec. 6, 2006; 2 pages.
Szeto; "Cell-permeable, Mitochondrial-targeted, Peptide Antioxidants"; The AAPS Journal 2006; 8(2): E277-E283.
Rao et al.; "Protective Effects of Phenyl-N-tert-butylnitrone on the Potentiation of Noise-Induced Hearing Loss by Carbon Monoxide"; Toxicology and Applied Pharmacology 167, 125-131 (2000).
Hu et al.; "R-phenylisopropyladenosine attenuates noise-induced hearing loss in the chinchilla"; Hearing Research 113 (1997) 198-206.
Kopke et al.; "Enhancing Intrinsic Cochlear Stress Defenses to Reduce Noise-Induced Hearing Loss"; The Laryngoscope 112: Sep. 2002; 1515-1532.
Kopke et al; "Prevention of impulse noise-induced hearing loss with antioxidants"; Acta Oto-Laryngologica, 2005; 125: 235-243.
Kopke et al; "Reduction of noise-induced hearing loss using L-NAC and salicylate in the chinchilla"; Hearing Research 149 (2000) 138-146.
Lynch et al; "Compounds for the prevention and treatment of noise-induced hearing loss"; DDT vol. 10, No. 19 Oct. 1996; 1291-1298.
Ohinata et al.; "Protection from noise-induced lipid peroxidation and hair cell loss in the cochlea"; Brain Research 966 (2003) 265-273.
Ohinata et al.; "Glutathione limits noise-induced hearing loss"; Hearing Research 146 (2000) 28-34.
Ohinata et al; "Intense noise induces formationof vasoactive lipid peroxidation products in the cochlea"; Brain Research 878 (2000) 163-173.
Seidman et al; "Effects of resveratrol on acoustic trauma"; Otolaryngology—Head and Neck Surgery Nov. 2003; vol. 129 No. 5; 463-470.
Seidman et al; "The protective effectsof alopurinol and superoxide dismutase on noise-induced cochlear damage"; Otolaryngology—Head and Neck Surgery Dec. 1993 vol. 109 No. 6; 1052-1056.
Seidman et al; "Biologic Activity of Mitochondrial Metabolites on Aging and Age-Related Hearing Loss"; The American Journal of Otology 2000 21:161-617.
Shoji et al.; "Glial cell line-derived neurotrophic factor has a dose dependent influence on noise-induced hearing loss in the guinea pig cochlea"; Hearing Research 142 (2000) 41-55.
Takemoto et al; "The clinical free radical scavenger, edaravone, protects cochlear hair cells from acoustic trauma"; European Journal of Pharmacology 487 (2004) 113-116.
Wang et al.; "A Peptide Inhibitor of c-Jun N-Terminal Kinase Protects against Both Aminoglycoside and Acoustic Trauma-Induced Auditory Hair Cell Death and Hearing Loss"; The Journal of Neuroscience, Sep. 17, 2003 23 (24):8596-8607.

(Continued)

*Primary Examiner* — Richard Schnizer
*Assistant Examiner* — Audrea Buckley
(74) *Attorney, Agent, or Firm* — McAfee & Taft

(57) ABSTRACT

The current invention provides methods and compositions for treating sensorineural hearing loss including but not limited to acute acoustic trauma (AAT). The composition includes compounds which function as free radical traps such as phenyl butyl nitrone (PBN), free radical scavengers, such as edaravone, resveratrol, ebselen and iron chelator and compounds from the family of antioxidant compounds including, but not limited to, N-acetylcysteine (NAC), Acetyl-L-Carnitine (ALCAR), glutathione monoethylester, ebselen, D-methionine and carbamathione. The compositions of the current invention may be delivered by injections or orally.

34 Claims, No Drawings

OTHER PUBLICATIONS

Wu et al.; "The Chemoprotective Agent N-Acetylcysteine Blocks Cisplatin-Induced Apoptosis through Caspase Signaling Pathway"; The Journal of Pharmacology and Experimental Therapeutics vol. 312, No. 2 (2005) 424-431.

Yamashita et al; "Delayed production of free radicals following noise exposure"; Brain Research 1019 (2004) 201-209.

Yamasoba et al; "Attenuation of cochlear damage from noise trauma by an iron chelator, a free radical scavenger and glial cell line-derived neurotrophic factor in vivo"; Brain Research 815 (1999) 317-325.

Yamasoba et al; "Ebselen prevents noise-induced excitotoxicity and temporary threshold shift"; Neuroscience Letters 380 (2005) 234-238.

Yamasoba et al; "Role of glutathione in protection against noise-induced hearing loss"; Brain Research 784 (1998) 82-90.

Ylikoski et al; Blockade of c-Jun N-terminal kinase pathway attenuates gentamicin-induced cochlear and vestibular hair cell death; Hearing Research 166 (2002) 33-43.

Moat et al; Recommended approaches for the laboratory measurement of homocysteine in the diagnosis and monitoring of patients with hyperhomocysteinaemia; Ann Clin Biochem 1999; 36: 372-379.

* cited by examiner

METHODS FOR TREATING ACUTE ACOUSTIC TRAUMA

CROSS RELATED

This application claims the benefit of previously filed International Application PCT/US2007/016758 filed Jul. 25, 2007, Provisional Application Ser. No. 60/833,452 filed on Jul. 26, 2006 and Provisional Application Ser. No. 60/833,114, filed on Jul. 25, 2006.

STATEMENT AS TO FEDERALLY SPONSORED RESEARCH

This application was supported in part by a contract from Office of Naval Research, Contract Number: N00014-05-1-0526. The United States Government may have rights in and to this application by virtue of this funding.

BACKGROUND OF THE INVENTION

Acute acoustic trauma (AAT) is known to cause permanent hearing loss. Hearing loss from AAT is also enhanced by simultaneous exposure to other toxins such as low levels of carbon monoxide or acrylonitrile. Recent studies indicate that free radical processes are involved in the AAT-induced hearing loss. At this time an FDA approved treatment does not exist for the treatment of AAT or other causes of sensorineural hearing loss (SNHL). Thus, a substantial need exists for treatment methods and compounds suitable for treating victims of AAT events. Additionally, a need exists for treatment of all forms of (SNHL).

SUMMARY OF THE INVENTION

In one embodiment, the current invention provides a method for treating sensorineural hearing loss. In the method of the current invention, a pharmaceutically effective amount effective amount of a composition selected from the group consisting of 4-hydroxy-α-phenyl butyl nitrone, derivatives of 4-hydroxy-α-phenyl butyl nitrone and phenyl-N-tert-butyl nitrone is administered to an organism having experienced sensorineural hearing loss. Optionally, the composition may further comprise one or more compounds selected from the group consisting of N-acetylcysteine, Acetyl-L-Carnitine, glutathione monoethylester, ebselen, D-methionine, carbamathione and Szeto-Schiller peptides and their functional analogs. Preferably, the composition for treating sensorineural hearing loss comprises 4-hydroxy-α-phenyl butyl nitrone, N-acetylcysteine and Acetyl-L-Carnitine. The compounds of the present invention are particularly useful when treating AAT-induced hearing loss.

In another embodiment, the present invention provides a composition for treating sensorineural hearing loss. The composition includes a first component comprising a pharmaceutically effective amount of a compound selected from the group consisting of 4-hydroxy-α-phenyl butyl nitrone, derivatives of 4-hydroxy-α-phenyl butyl nitrone and phenyl-N-tert-butyl nitrone. The composition also includes a second component comprising a pharmaceutically effective amount of a compound selected from the group consisting of: Acetyl-L-Carnitine, glutathione monoethylester, ebselen, D-methionine, carbamathione and Szeto-Schiller peptides and their functional analogs. Finally, the composition includes a third component comprising a pharmaceutically effective amount of N-acetylcysteine.

In an alternative embodiment, the current invention provides a composition for treating sensorineural hearing loss. This composition comprises a pharmaceutically effective amount of a compound selected from the group consisting of 4-hydroxy-α-phenyl butyl nitrone, derivatives of 4-hydroxy-α-phenyl butyl nitrone and phenyl-N-tert-butyl nitrone. Optionally, the composition may include at least one antioxidant such as N-acetylcysteine, Acetyl-L-Carnitine, glutathione monoethylester, ebselen, D-methionine, carbamathione and Szeto-Schiller peptides and their functional analogs. These chemicals may be compounded and formulated such that in different fixed optimal ratios two or more chemicals are contained in a single solution, capsule, pill, matrix, or particle to be ingested, injected or delivered to the treatment subject at one time.

DETAILED DESCRIPTION OF THE PREFERRED EMBODIMENTS OF THE CURRENT INVENTION

This invention provides methods for treating sensorineural hearing loss resulting from AAT and likely other causes of deafness related to oxidative stress, programmed cell death, or inflammatory processes. Examples of other causes of SNHL include but are not limited to, age related hearing loss or presbyacusis, toxin-induced hearing loss, trauma induced hearing loss, viral or bacterial infection leading to hearing loss, hearing loss due to prematurity, hearing loss due to cochlear ischemia, congenital hearing loss, genetic hearing loss, Meniere's disease, sudden hearing loss, and hearing loss related to thyroid disorders or diabetes mellitus. The current invention demonstrates the functionality of compounds which function as free radical traps such as phenyl butyl nitrone (PBN), free radical scavengers, such as edaravone, resveratrol, ebselen and iron chelator and compounds from the family of antioxidant compounds including, but not limited to, N-acetylcysteine (NAC), Acetyl-L-Carnitine (AL-CAR), glutathione monoethylester, ebselen, D-methionine and carbamathione in the treatment of AAT.

Additionally, antioxidant peptides, which target the mitochondria, are useful in the present invention. These compounds preclude the generation of intracellular reactive oxygen species (ROS) which leads to oxidative stress and damage of the mitochondria. Oxidative damage of the mitochondria is known to cause apoptosis and necrosis leading to cell death. The preferred antioxidant peptides are Szeto-Schiller (SS) peptides and their functional analogs. These compounds have alternating aromatic residues and basic amino acids. In particular, peptides having tyrosine (Tyr) or dimethyltyrosine (Dmt) analogs can scavenge oxyradicals. These compounds inhibit oxidation of low-density lipoproteins. SS-peptides include compounds such as SS-31 (D-Arg-Dmt-Lys-Phe- NH$_2$) and SS-02 (Dmt-D-Arg-Phe-Lys-NH$_2$). In addition to the Tyr and Dmt containing SS-peptides, tryptophan containing SS-peptides are also useful in the current invention. Finally, the amino acids found in the SS-peptides may be L or D and may be naturally occurring, non-naturally occurring and derivatives of naturally occurring amino acids. In particular, the SS-peptides disclosed in PCT published application WO 2005/072295 are suitable for use in the current invention. The entire disclosure of WO 2005/072295, published on Aug. 11, 2005 is incorporated herein by reference.

Thus, the current invention provides methods and compositions suitable for treating the referenced hearing conditions. In a preferred embodiment, the current invention utilizes 4-hydroxy-α-phenyl butyl nitrone (4-OHPBN) or a derivative of 4-OHPBN alone or in combination with at least one antioxidant to treat AAT. Additionally, phenyl-N-tert-butyl nitrone (PBN) and derivatives thereof will be useful in the current invention. The treatment may be administered orally, intravenously, subcutaneously, by inhalation, sublingually, subdermally or locally within the ear, and administered as a nanoparticle or dendrimer formulation, the nanoparticle may be multifunctional and composed of a polymer and paramagnetic iron oxide particles to allow the application of external magnetic forces to aid in the delivery of the drug to the desired target such as the inner ear. Additionally, the derivatives of the 4-OHPBN may be formulated to enhance oral absorbtion, alter bioavailability kinetics, and/or formulated in a combination with one or more of the above compounds. Preferably, the compositions for treating AAT will be administered orally. However, other methods which deliver the compositions for treating AAT systemically to the body should work equally well.

We have discovered that a nitrone, 4-hydroxy-α-phenyl butyl nitrone (4-OHPBN), administered in combination with the antioxidant N-acetylcysteine (NAC) four hours after a six hour period of noise exposure (AAT event) that would have caused permanent hearing loss completely prevented any loss of hearing. Further, as demonstrated by the accompanying Figures, administration of 4-OHPBN four hours after AAT prevented the normally expected permanent hearing loss. Without wishing to be limited by theory, we believe that at least part of the functionality of 4-OHPBN results from its ability to inhibit the activity or up regulation of inducible nitric oxide synthase (INOS). INOS is responsible for activating neural inflammation which may increase the effect of oxidative stress or other injury to the inner ear tissues.

Tables 1-A, 1-B, 1-C, 2 and 3 illustrate the results obtained using the compositions of the current invention. Table 1-A demonstrates that use of 4-OHPBN in a dose-effect manner prevents hearing loss in chinchillas when administered as an intraperitoneal (i.p.) injection four hours after exposure to noise sufficient to constitute AAT. Table 1-B and 1-C demonstrate the effects achieved by the antioxidants ALCAR and NAC for comparison with the 4-OHPBN treatments. Table 3 demonstrates the results when using the combination of NAC (100 mg/1 kg) and 4-OHPBN (50 mg/kg) administered four hours after an AAT event. As depicted, the treatment completely prevented hearing loss in the test animals. In each instance, dosage amounts are given in mg per kg of the test subject. Further, the following test results demonstrate the improvements provided by 4-OHPBN, alone and in combination with other compounds, over the combination of NAC plus ALCAR.

The following experimental data demonstrates the benefits of the current invention. With reference first to Tables 1-A, 1-B and 1-C, tests were conducted using six chinchillas for each experimental group and the control group. In these tests, the animals were exposed to AAT generated by six hours of noise exposure at 4 kHz octave band noise at 105 dB SPL. Treatments using 4-OHPBN (dosages of 10, 20, 50, and 75 mg/kg), ALCAR (dosages of 0, 20, 30, and 50 mg/kg), and NAC (50, 100, and 200 mg/kg) were given four hours after the AAT by intraperitoneal injection. Hearing levels were determined by auditory brainstem response (ABR) prior to the AAT event (baseline) and at 21 days post injection.

TABLE 1-A

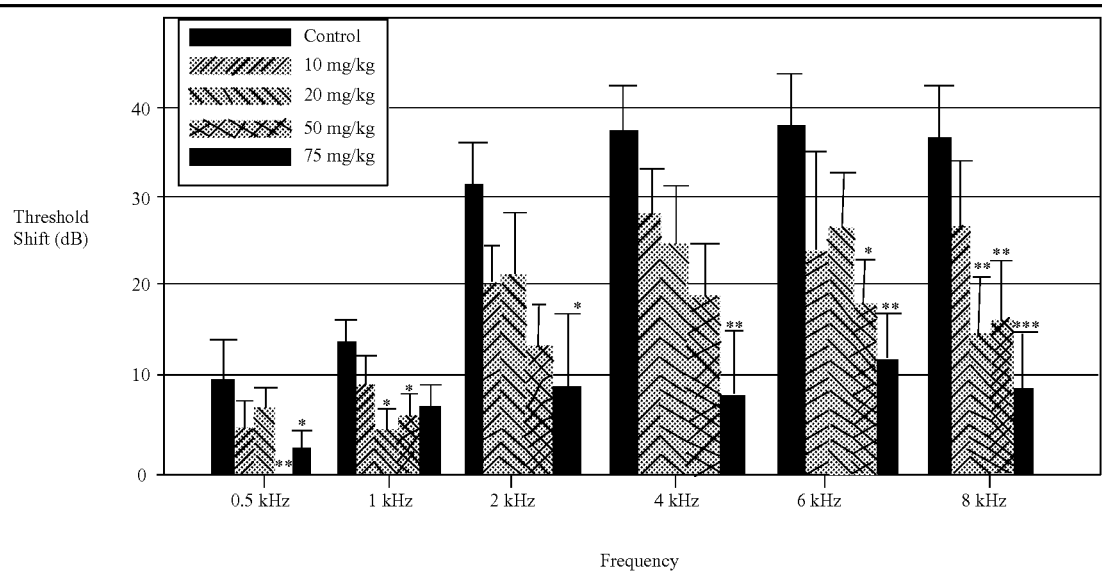

TABLE 1-B

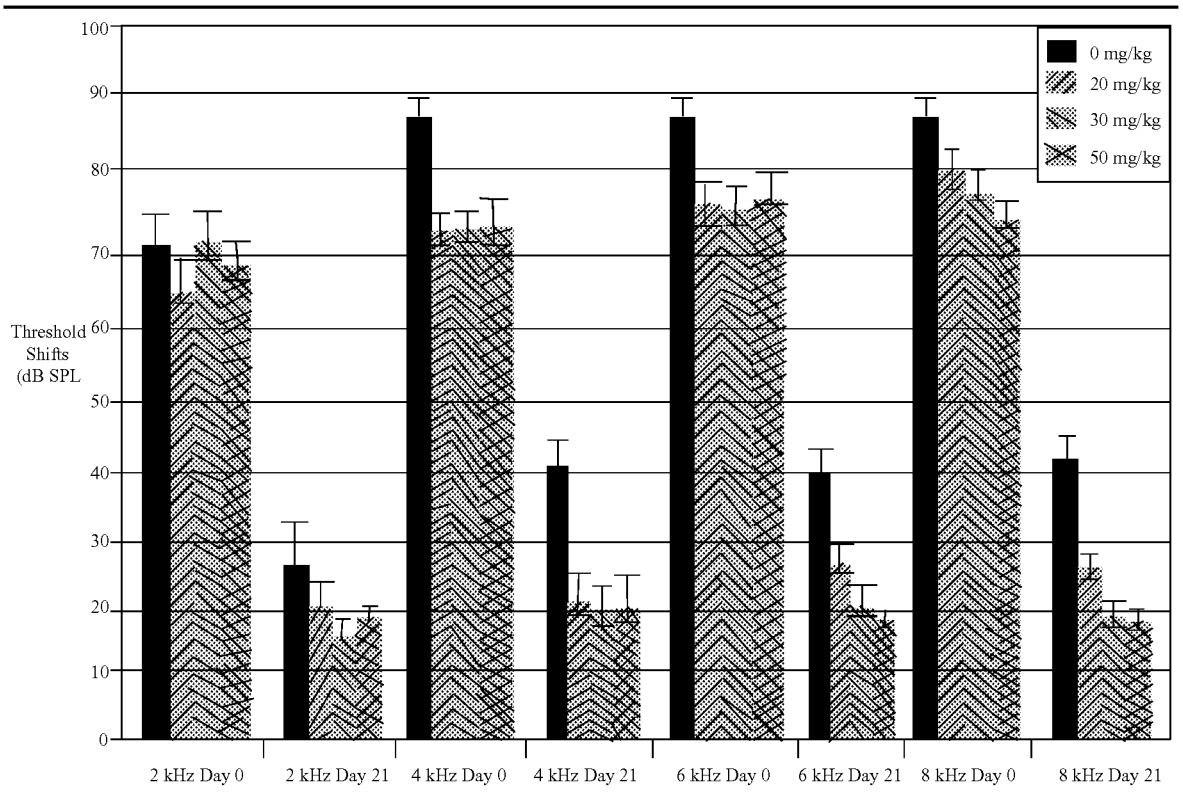

TABLE 1-C

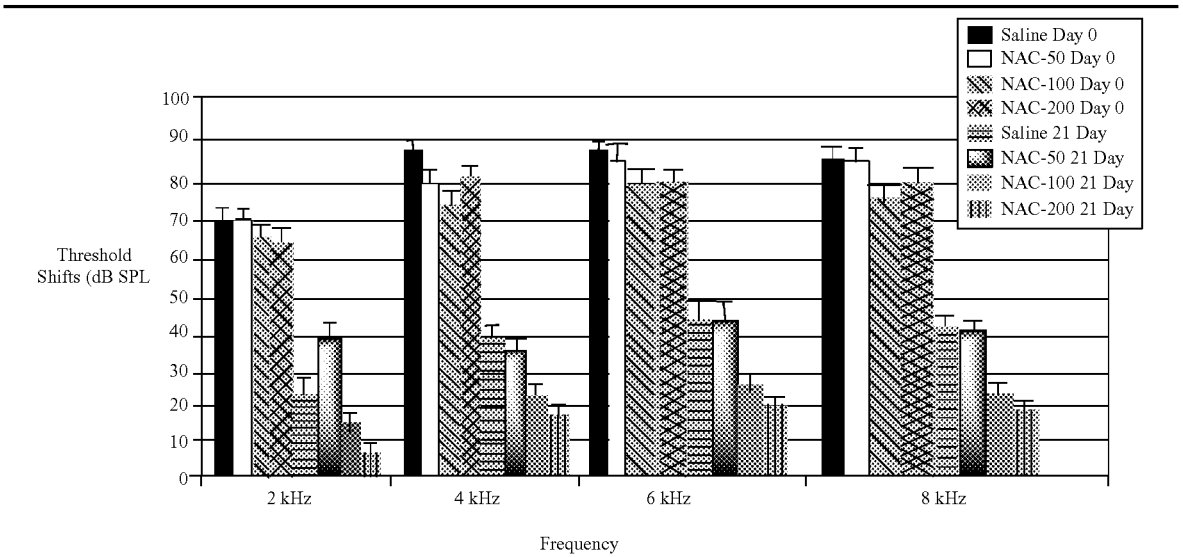

Note, in Table 1-A, the bar chart represents the following dosages, in order, for each indicated frequency: control 0.0 mg/kg, 10 mg/kg, 20 mg/kg, 50 mg/kg and 75 mg/kg. In Table 1-B the bar chart represents the following dosages in order for each indicated frequency and day: 0 mg/kg, 20 mg/kg, 30 mg/kg and 50 mg/kg. Finally, in Table 1-C, the bar chart represents the following dosages in order for each indicated frequency: control (saline), 50 mg/kg @ day 0, 10 mg/kg @ day 0, 200 mg/kg day @0, control (saline) @ day 21, 50 mg/kg @ day 21, 10 mg/kg @ day 21, 200 mg/kg @ day 21.

Table 1-A demonstrates the effectiveness of 4-OHPBN at each dosage level when compared to the control. In particular statistically significant results were obtained at the 50 mg/kg and 75 mg/kg dosages. As depicted by the * in Table 1-A, statistical analysis using a two way ANOVA and Post hoc test indicated a $p<0.05$ for dosages of 75 mg/kg at every tested frequency except 0.5 kHz. Since a p of less than 0.05 statistically represents a true effect and not a random result, the improvements reflected in Table 1-A clearly resulted from the administration of the 4-OHPBN. Effective results should be realized at dosages between 1 mg/kg and about 150 mg/kg for 4-OHPBN.

Table 1-B demonstrates the effectiveness of ALCAR at each dosage level when compared to the control with significant benefits provided by dosages of 30 mg/kg and 50 mg/kg. As depicted by the * in Table 1-B, statistical analysis using a two way ANOVA and Post hoc test indicated a $p<0.05$ for dosages of 30 mg/kg and 50 mg/kg at every tested frequency. Thus, the improvements reflected in Table 1-B clearly resulted from the administration of the ALCAR.

Table 1-C demonstrates the effectiveness of NAC when compared to the control with significant benefits provided by dosages of 100 mg/kg and 200 mg/kg. As depicted by the * in Table 1-C, statistical analysis using a two way ANOVA and Post hoc test indicated a $p<0.05$ for dosages of 100 mg/kg and 200 mg/kg at every tested frequency. Thus, the improvements reflected in Table 1-C clearly resulted from the administration of the NAC.

Table 2a demonstrates the effects of ALCAR and/or NAC on noise-induced threshold shift. Values are mean±SE dB SPL threshold shift from the baseline values to those 3 weeks after noise exposure. * Represents significant difference at $p<0.05$ (treated vs. control).  Represents significant difference at $p<0.01$ (treated vs. control). *Represents significant difference at $p<0.001$ (treated vs. control).

TABLE 2a

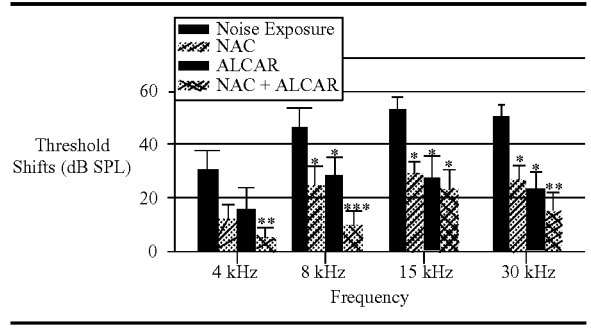

Test results represented in Tables 2a and 2b were generated using Male Sprague-Dawley rats, 200-300 g randomized into 5 groups, with 6 in each group except the no noise control (n=2). These groups were classified as follows: 1) no noise control (data not shown), 2) noise exposure with saline injection, 3) noise exposure with NAC (200 mg/kg) injection, 4) noise exposure with ALCAR (100 mg/kg) injection, and 5) noise exposure with NAC (200 mg/kg)+ALCAR (100 mg/kg) injection.

The test animals were prepared for the tests using ketamine (100 mg/kg) and xylazine (10 mg/kg) anesthesia. The animals were ABR tested for baseline hearing, immediate after noise exposure, 1, 2, and 3 weeks after noise exposure with an Intelligent Hearing System ABR system. ABR thresholds were obtained from subcutaneous needle electrodes placed under the skin of the head. The recording electrode was placed proximal to the right ears, the indifferent electrode was placed proximal to the left ear, and the ground electrode was placed at the vortex. Pure tones of 4, 8, 15, and 30 kHz were presented as stimuli through a high frequency transducer (ranging 2-32 kHz). The evoked responses recorded were an average of 1024 sweeps for each level tested. Hearing thresholds were tested at 10 dB descending steps until near the threshold, then, 5 dB steps were taken to determine the thresholds. Threshold was defined as the mid point between the lowest level of a clear response and next level no response was observed.

Noise exposure was carried out in an Industrial Acoustics Company sound isolation booth. The narrow band noise was generated by a Tucker-Davis Technologies real time processor (RP2) filtered and attenuated through a Tucker Davis Technology Acoustic system, then amplified by a Parasound high wattage amplifier, which drives two 8Ω Vifa speakers. Awake rats were put in wire-mesh cages located 5 inches below the speakers and were exposed to a narrow band noise centered at 13.6 kHz, 105 dB SPL for 80 minutes. The noise level was calibrated with a B&K 2209 sound level meter before each noise exposure.

The test animals received intraperitoneal injection 48 hours before, 1 hour after noise exposure, and twice a day for 2 additional days. For NAC, Mucomyst from Bristol-Myers Squibb, a commercially available solution was used for the injection. ALCAR was freshly made (dissolved in sterile saline) before each injection.

The indicated results in the graphs were obtained using two-way ANOVA statistical analysis. The LSD post-hoc test was used to determine significant differences among control and experimental groups.

TABLE 2b

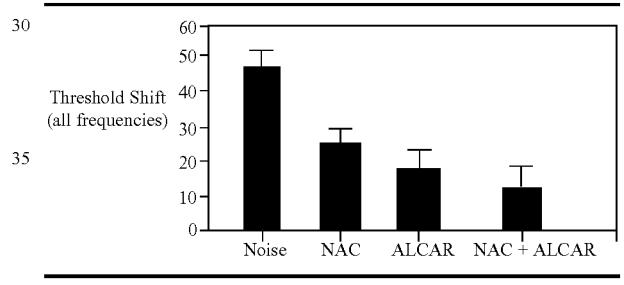

Table 2b demonstrates the effects of ALCAR and/or NAC on noise-induced threshold shift, plotted with average threshold shift data from all frequencies. Values are mean±SE dB SPL threshold shift from the baseline values to those observed three weeks after noise exposure. Differences between each treatment compared to noise only control were significant at $p<0.001$ (with t-test). Difference between NAC and NAC+ALCAR was significant at $p<0.01$ (with t-test). While the above tests were conducted at the specified dosages, effective results should be realized at dosages between about 5 mg/kg and about 500 mg/kg for NAC when used alone, between about 5 mg/kg and about 300 mg/kg for ALCAR when used alone, and between about 5 mg/kg and about 500 mg/kg for NAC and between about 5 mg/kg and about 500 mg/kg for ALCAR when NAC and ALCAR are used in combination.

Table 3 depicts the results provided by treatment with a preferred embodiment of the current invention. In this embodiment, the AAT treatment therapy utilized a combination of 4-OHPBN (50 mg/kg) with NAC (100 mg/kg). Treatment consisted of intraperitoneal injection of the combined 4-OHPBN and NAC four hours after the AAT event. In this instance, six chinchillas were used for each test group. The animals were exposed to an AAT event produced by six hours of noise exposure at 4 kHz octave band noise at 105 dB SPL. Hearing levels reported in Table 3 were determined using the ABR method prior to the AAT event and 21 days post AAT. As shown in Table 3, twenty one days post AAT the test animals experienced very little if any hearing loss. As indicated by the * each result was determined to be statistically significant and resulting from the treatment with the combination of 4-OHPBN and NAC. Statistical analysis was carried out using a one way ANOVA procedure and Post hoc test. While the above tests were conducted at the specified dosages, effective results should be realized at dosages between about 5 mg/kg and about 300 mg/kg for NAC and about 5 mg/kg and about 150 mg/kg for 4-OHPBN when NAC and 4-OHPBN are used in combination.

TABLE 3

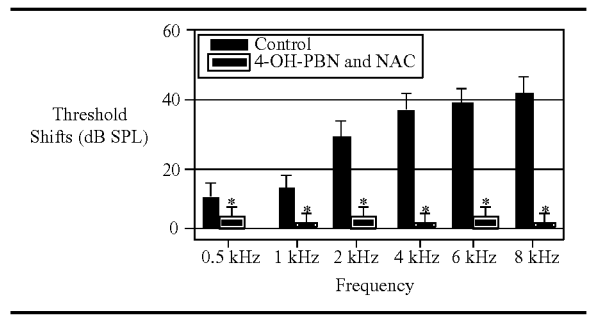

Table 4 depicts the results provided by treatment with another preferred embodiment of the current invention. The test for this embodiment utilized three test groups consisting of six chinchillas each. The chinchillas were exposed to an AAT event generated by a 105 dB narrow-band noise centered at 4 kHz for 6 hours. In this embodiment, the AAT treatment therapy utilized a combination of 4-OHPBN (20 mg/kg) with NAC (50 mg/kg) and ALCAR (20 mg/kg). Treatment consisted of intraperitoneal injection of the combined 4-OHPBN, NAC and ALCAR beginning four hours after noise exposure with injections repeated twice daily for the next two days. The control group was injected with carrier solution. Hearing levels reported in Table 4 were determined using the ABR method prior to the AAT event, immediately after the AAT event and 21 days after the AAT event.

TABLE 4

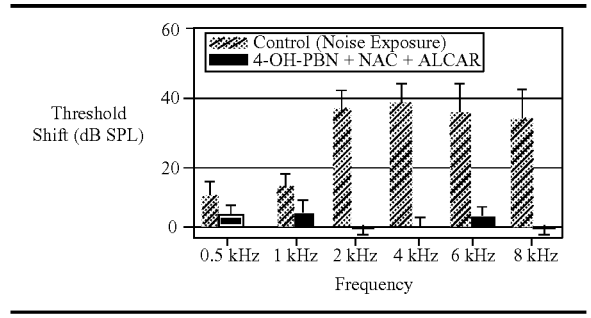

As shown in Table 4, twenty one days post AAT the test animals experienced zero hearing loss. Mean ABR threshold shifts were obtained and statistically analyzed using a two-way ANOVA procedure. Thus, the drug combination of this embodiment completely eliminated permanent threshold shifts thereby precluding hearing loss.

The effective dose of each agent in the three drug combination was approximately half that of the two drug 4-OHPBN/NAC combination. Further, the concentration of the individual drugs in the three drug combination was significantly lower than the concentration necessary when each compound is used individually. Thus, these results demonstrate that combinations of antioxidants can effectively treat acute acoustic trauma. Further, the test results indicate a synergistic effect resulting from the combination of the indicated compounds. Thus, combination therapy will likely increase the effectiveness of treatment and decrease the required medication dose.

While the above tests were conducted at the specified dosages, effective results should be realized at dosages between about 5 mg/kg and about 300 mg/kg for NAC, between about 5 mg/kg and about 150 mg/kg for 4-OHPBN and between about 5 mg/kg and about 500 mg/kg for ALCAR when ALCAR, NAC and 4-OHPBN are used in combination.

In general it is expected that treatment of AAT hearing loss should begin as soon as possible. For treatment of other types of sensorineural hearing loss treatment using the methods and compositions described herein will vary depending on the cause of hearing loss. For example hearing loss due to age may require delivery of one of the above described compositions on a regular treatment schedule such daily, alternating days or weekly depending on the nature of the hearing loss. In cases relating to hearing loss resulting from toxins or radiation, treatment should begin as soon as possible and will likely conclude upon restoration of hearing.

The current disclosure demonstrates the effectiveness of 4-OHPBN alone and in combination with NAC at preventing hearing loss resulting from AAT. Additionally, the effectiveness of NAC and ALCAR alone or in combination with each other has been demonstrated. Further, this disclosure demonstrates the effectiveness of the combination of ALCAR, 4-OHPBN and NAC. One skilled in the art from a reading of this disclosure will likely recognize related compounds which will also provide satisfactory results. Further, although the foregoing examples treated the test subjects four hours post AAT, treatments administered within shorter time periods should be as effective and will likely be preferred. In addition, treatments administered longer than 24 hour post AAT, stress or injury may also be effective. As such the foregoing disclosure is merely considered to be exemplary of the current invention with the true scope of the current invention being defined by the claims.

We claim:

1. A method for treating sensorineural hearing loss comprising:
   delivering to an organism which has experienced sensorineural hearing loss a pharmaceutically effective amount of a composition comprising 4-hydroxy-α-phenyl butyl nitrone.

2. The method of claim 1, wherein the step of delivering is carried out by a method selected from the group consisting of orally, intravenously, subcutaneously, by inhalation, sublingually, subdermally or injection locally within the ear.

3. The method of claim 1, further comprising incorporating an anti-oxidant in said composition.

4. The method of claim 3, wherein said anti-oxidant is selected from the group consisting of: N-acetylcysteine, acetyl-L-carnitine, glutathione monoethylester, ebselen, D-methionine, carbamathione and Szeto-Schiller peptides.

5. The method of claim 3, wherein said anti-oxidant comprises N-acetylcysteine.

6. The method of claim 5, wherein said method is used to treat acute acoustic trauma.

7. The method of claim 6, wherein said composition is initially administered within four hours of an acute acoustic trauma event.

8. The method of claim 6, further comprising delivering said composition twice in a twenty-four hour period.

9. The method of claim 5, wherein said composition comprises from about 1 mg/kg to about 150 mg/kg of 4-hydroxy-α-phenyl butyl nitrone.

10. The method of claim 5, wherein said composition comprises from about 5 mg/kg to about 300 mg/kg of N-acetylcysteine.

11. The method of claim 5, wherein said composition further comprises acetyl-L-carnitine.

12. The method of claim 11, wherein said composition comprises from about 5 mg/kg to about 500 mg/kg of acetyl-L-carnitine.

13. A method for treating sensorineural hearing loss comprising:
    delivering to an organism which has experienced sensorineural hearing loss a pharmaceutically effective amount of a composition comprising a first component comprising a pharmaceutically effective amount of 4-hydroxy-α-phenyl butyl nitrone, a second component comprising a pharmaceutically effective amount of a compound selected from the group consisting of acetyl-L-carnitine, glutathione monoethylester, ebselen, D-methionine, carbamathione and Szeto-Schiller peptides, and a third component comprising N-acetylcysteine.

14. The method of claim 13, wherein said composition comprises from about 5 mg/kg to about 150 mg/kg of 4-hydroxy-α-phenyl butyl nitrone, from about 5 mg/kg to about 300 mg/kg of N-acetylcysteine and from about 5 mg/kg to about 500 mg/kg of acetyl-L-carnitine.

15. The method of claim 13, wherein said method is used to treat acute acoustic trauma.

16. The method of claim 15, wherein said composition is initially administered within four hours of an acute acoustic trauma event.

17. The method of claim 15, further comprising delivering said composition twice in a twenty-four hour period.

18. The method of claim 13, wherein said composition is delivered orally on a daily basis.

19. A method for treating sensorineural hearing loss comprising:
    delivering to an organism which has experienced sensorineural hearing loss a pharmaceutically effective amount of a composition comprising 4-hydroxy-α-phenyl butyl nitrone and N-acetylcysteine.

20. The method of claim 19, wherein said composition comprises from about 5 mg/kg to about 150 mg/kg of 4-hydroxy-α-phenyl butyl nitrone and from about 5 mg/kg to about 300 mg/kg of N-acetylcysteine.

21. The method of claim 19, wherein said method is used to treat acute acoustic trauma.

22. The method of claim 21, wherein said composition is initially administered within four hours of an acute acoustic trauma event.

23. The method of claim 22, further comprising delivering said composition twice in a twenty-four hour period.

24. A method of preventing oxidative damage to mitochondria comprising:
    delivering to an organism a pharmaceutically effective amount of a composition consisting of 4-hydroxy-α-phenyl butyl nitrone.

25. The method of claim 24, further comprising incorporating an anti-oxidant in said composition, wherein said anti-oxidant is selected from the group consisting of: N-acetylcysteine, acetyl-L-carnitine, glutathione monoethylester, ebselen, D-methionine, carbamathione and Szeto-Schiller peptides.

26. The method of claim 24, wherein said composition further comprises N-acetylcysteine.

27. The method of claim 26, wherein said composition comprises from about 5 mg/kg to about 300 mg/kg of N-acetylcysteine.

28. The method of claim 26, wherein said composition further comprises acetyl-L-carnitine.

29. The method of claim 28, wherein said composition comprises from about 5 mg/kg to about 500 mg/kg of acetyl-L-carnitine.

30. A method of preventing oxidative damage to mitochondria comprising:
    delivering to an organism a pharmaceutically effective amount of a composition comprising N-acetylcysteine and 4-hydroxy-α-phenyl butyl nitrone.

31. A composition comprising:
    a first component comprising 4-hydroxy-α-phenyl butyl nitrone; and,
    a second component comprising a compound selected from the group consisting of N-acetylcysteine, acetyl-L-carnitine, glutathione monoethylester, ebselen, D-methionine, carbamathione and Szeto-Schiller peptides,
    wherein the composition has a sufficient amount of each component to render the composition pharmaceutically effective to treat sensorineural hearing loss.

32. The composition of claim 31, wherein the second component is N-acetylcysteine.

33. A composition comprising:
    a first component comprising 4-hydroxy-α-phenyl butyl nitrone; a second component comprising a compound selected from the group consisting of acetyl-L-carnitine, glutathione monoethylester, ebselen, D-methionine, carbamathione and Szeto-Schiller peptides; and,
    a third component comprising a pharmaceutically effective amount of N-acetylcysteine,
    wherein the composition has a sufficient amount of each component to render the composition pharmaceutically effective to treat sensorineural hearing loss.

34. The composition of claim 32 further comprising a third component, the third component comprising a compound selected from the group consisting of acetyl-L-carnitine, glutathione monoethylester, ebselen, D-methionine, carbamathione and Szeto-Schiller peptides,
    wherein the composition has a sufficient amount of each component to render the composition pharmaceutically effective to treat sensorineural hearing loss.

* * * * *